US009606048B2

United States Patent
Kumar et al.

(10) Patent No.: US 9,606,048 B2
(45) Date of Patent: Mar. 28, 2017

(54) METHOD FOR DETERMINING THE WEIGHT AND THICKNESS OF A PASSIVATION OR CONVERSION COATING ON A SUBSTRATE

(71) Applicant: Momentive Performance Materials Inc., Waterford, NY (US)

(72) Inventors: Vikram Kumar, Tarrytown, NY (US); Lesley Hwang, Chappaqua, NY (US); Kujtim Bizati, Tarrytown, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/319,626

(22) Filed: Jun. 30, 2014

(65) Prior Publication Data

US 2015/0377608 A1 Dec. 31, 2015

(51) Int. Cl.
| | |
|---|---|
| *G01N 21/17* | (2006.01) |
| *G01G 7/00* | (2006.01) |
| *G01B 11/06* | (2006.01) |
| *G01N 21/3563* | (2014.01) |
| *G01N 21/84* | (2006.01) |

(52) U.S. Cl.
CPC ......... *G01N 21/17* (2013.01); *G01B 11/0616* (2013.01); *G01G 7/00* (2013.01); *G01N 21/3563* (2013.01); *G01N 21/8422* (2013.01)

(58) Field of Classification Search
CPC .......... G01N 2021/3595; G01N 21/17; G01N 21/3563; G01N 21/8422; G01B 11/06; G01G 7/00
USPC ................... 250/339.08, 358.1, 359.1, 252.1
See application file for complete search history.

(56) References Cited

U.S. PATENT DOCUMENTS

| 4,943,721 A * | 7/1990 | Vidrine, Jr. .................. 850/63 |
| 4,946,902 A * | 8/1990 | Bekiarian et al. ......... 525/326.2 |
| 5,821,001 A * | 10/1998 | Arbab et al. .................. 428/623 |
| 6,573,999 B1 * | 6/2003 | Yang ............................. 356/632 |
| 6,895,360 B2 | 5/2005 | Liu et al. |
| 7,071,174 B1 * | 7/2006 | Lange et al. .................... 514/55 |
| 2002/0041967 A1 * | 4/2002 | Nakamura et al. ........... 428/432 |
| 2003/0024432 A1 | 2/2003 | Chung et al. |
| 2003/0230720 A1 | 12/2003 | Shelley et al. |
| 2004/0117146 A1 * | 6/2004 | Liu et al. ....................... 702/172 |
| 2004/0155190 A1 | 8/2004 | Shelley et al. |
| 2005/0229698 A1 * | 10/2005 | Beecroft et al. ................ 73/300 |
| 2006/0228470 A1 * | 10/2006 | He et al. ....................... 427/180 |

(Continued)

FOREIGN PATENT DOCUMENTS

DE 102006052114 5/2008

OTHER PUBLICATIONS

Balachandran et al. (2010), "Synthesis of Nano TiO2—SiO2 Composite using Sol-Gel Method: Effect on Size, Surface Morphology and Thermal Stability", International Journal of Engineering Science and Technology 2(8): 3695-3700.

(Continued)

*Primary Examiner* — David Porta
*Assistant Examiner* — Blake Riddick
(74) *Attorney, Agent, or Firm* — James C. Abruzzo

(57) ABSTRACT

The present invention relates to a method for measuring the weight of a passivation coating composition on a moving substrate with minimal interruption. The method of present invention is especially useful for effective quality control in an industrial setting.

20 Claims, 1 Drawing Sheet

FTIR Signal Correlation with One Second of Acquisition Time for Calibration Standards # 2-5.

(56) References Cited

U.S. PATENT DOCUMENTS

| | | | |
|---|---|---|---|
| 2008/0210343 A1* | 9/2008 | Ebert et al. | 148/284 |
| 2011/0059867 A1* | 3/2011 | Kim et al. | 506/16 |
| 2012/0107625 A1* | 5/2012 | Smith et al. | 428/447 |
| 2013/0125961 A1* | 5/2013 | Sun et al. | 136/252 |
| 2014/0017409 A1* | 1/2014 | Kulkarni et al. | 427/343 |
| 2014/0088876 A1* | 3/2014 | Shiley et al. | 702/8 |
| 2014/0202233 A1* | 7/2014 | Itaya et al. | 73/23.31 |
| 2014/0342164 A1* | 11/2014 | Hwang | 428/447 |

OTHER PUBLICATIONS

International Search Report and Written Opinion from PCT/US2015/037642 dated Oct. 2, 2015.

\* cited by examiner

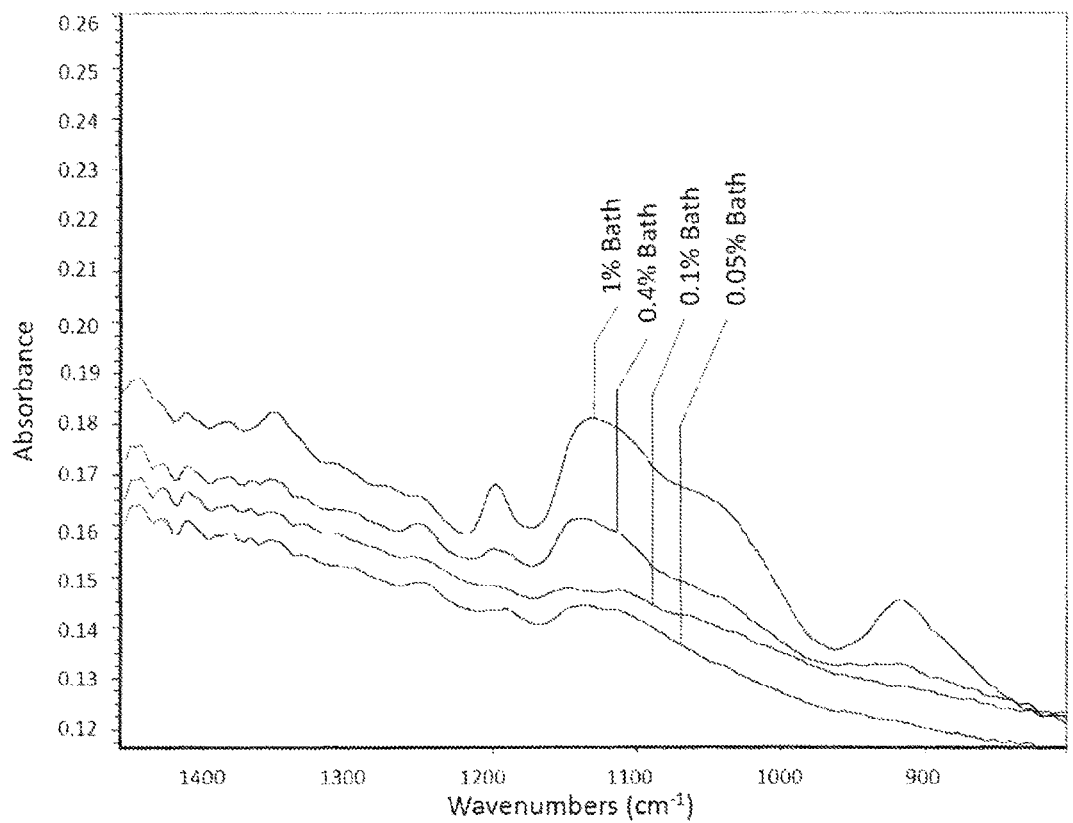
FTIR Signal Correlation with One Second of Acquisition Time for Calibration Standards # 2-5.

METHOD FOR DETERMINING THE WEIGHT AND THICKNESS OF A PASSIVATION OR CONVERSION COATING ON A SUBSTRATE

BACKGROUND OF THE INVENTION

1. Field of the Invention

The present invention relates to a method for determining the weight and thickness of a passivation coating composition on a substrate. Particularly, the invention relates to a passivation coating composition on a metal substrate wherein the metal substrate is a moving coil line.

2. Description of Related Art

A variety of commercial passivation coating compositions are known for preparing metal surfaces to prevent corrosion and improve adhesion of paints or other coatings to the surface. For example, silane pretreatment coatings are used in commercial applications to provide anticorrosion properties to metal surfaces and/or to prepare the metal surfaces prior to painting operations. However, silane pretreatments are extremely difficult to detect by human visual inspection because silane pretreatments are colorless when applied, and at very low coating weights.

Methods for determining the presence of thin films on a substrate are known. Certain fluorescent dyes in metal film coatings have been used to determine whether or not the coating has been applied to the surface. Specifically, the fluorescent brightening agents stilbene and coumarin are added to a chrome-free metal coating and, after covering the metal with the coating, the metal is viewed under ultraviolet (UV) light and the presence of coating is detected by eye. The methods are useful in their ability to determine whether a coating has been applied to a substrate. The methods have been developed which involve quantitative determination of the thickness of the coating, an important quality control matter. Although possible, use of stilbene and coumarin in quantitative determinations of thickness of a coating is not preferred because it has been found that these compounds often do not display the required precision in their use in a calibrated system to determine coating thickness that is required in a commercially feasible coating thickness measurement system. The native fluorescence of the coating can interfere with measurement of fluorescent intensity of the coating.

Methods for determining thickness of transparent oil films on metal surfaces by detection of fluorescent compounds mixed in the oil are also known. However, due to the nature of oil films, these methods are not precise and, therefore, are not suitably reproducible for determination of the thickness of a dryable, dried, curable or cured film-forming coating on a substrate. The layer of oil is typically not maintained on the surface of the substrate if additional layers of a coating are needed on the oil-covered substrate, such as a pre-coating, a primer or a color coat.

It is more difficult to determine the weight and thickness of a passivation coating composition on a moving substrate, for example, a moving coil line, without significantly interrupting the movement of the substrate.

Accordingly, there is a need to be able to quickly detect the presence, weight and thickness of the passivation coating composition as an essential aspect of quality control.

SUMMARY OF THE INVENTION

In accordance with one aspect of the invention, there is provided a method for measuring the weight of a passivation coating composition on a substrate comprising the steps of:

(i) applying a passivation coating composition on a substrate to obtain a sample passivation coating composition;

(ii) measuring a Fourier Transform Infrared energy spectrum of the sample passivation coating composition;

(iii) obtaining a calibration standard using a Fourier Transform Infrared energy spectrum of one or more calibration samples having a predetermined weight of the passivation coating composition on the substrate; and, (iv) comparing the Fourier Transform Infrared energy spectrum with the calibration standard to result in a measurement of the weight of the sample passivation coating composition on the substrate.

The method of the present invention provides accurate measurements of the weight and thickness of a moving substrate with minimal interruption. The method of present invention is especially useful for effective quality control in an industrial setting.

BRIEF DESCRIPTION OF THE FIGURE

FIG. 1 shows FTIR signal correlation with one second of acquisition time of calibration standards #2-5.

DETAILED DESCRIPTION OF PREFERRED EMBODIMENTS

In the specification and claims herein, the following terms and expressions are to be understood as indicated herein below.

It will also be understood that any numerical range recited herein is intended to include all sub-ranges within that range and any combination of end points of said ranges or sub-ranges.

All methods described herein may be performed in any suitable order unless otherwise indicated or clearly contrary to context. The use herein of any and all examples or exemplification language (for example, such as), is intended merely to better illustrate the invention and does not pose a limitation on the scope of the invention unless otherwise claimed. No language in the specification should be construed as indicating any non-claimed element as essential to the practice of the invention.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

As used herein, the term "bare metal" refers to metal surfaces that have not been treated with the conversion or passivation coating composition of the invention and have not been painted. As used herein, the expression "passivation coating" shall be understood to be synonymous with "conversion coating".

It will be understood herein that any known or commercially used passivation coating composition can be employed herein. Examples of passivation coating compositions include silane-containing coatings, metal alkoxide coatings, such as titanium tetraethoxide and zirconium tetraethoxide, fluorozirconic acid coatings and fluorotitanic acid coatings.

A silane-containing coating is a coating composition comprising at least one compound selected from the group consisting of organofunctional silane, hydrolyzate of the organofunctional silane and condensate of the organofunctional silane. It will be understood herein that the silane-containing coating composition can include a mixture of two or more compounds selected from the group consisting of organofunctional silanes, hydrolyzates and condensates.

In one embodiment, the silane-containing coating composition contains an organofunctional silane having the general Formula (I):

wherein X is an organofunctional group of valence, including mono-, di- or polyvalent groups; each occurrence of $R^1$ is independently a linear, branched or cyclic divalent organic group of up to 12 carbon atoms, more specifically up to 10 carbon atoms, and most specifically from up to 8 carbon atoms and optionally containing one or more heteroatoms, such as the non-limiting examples of O, N, P, Cl, Br, I and S, with the proviso that X and the silicon atom of the silyl group are bonded to the $R^1$ group through a covalent bond to a carbon atom of $R^1$, thereby forming a bridge between organofunctional group X and the silyl group; each occurrence of $R^2$ is independently an alkyl, alkoxy-substituted alkyl, aryl, or aralkyl, each containing up to 16 carbon atoms, more specifically from up to 12 carbon atoms and most specifically from up to 8 carbon atoms; each $R^3$ is independently an acetyl, alkyl, or alkoxy-substituted alkyl, each containing up to 16 carbon atoms, more specifically up to 12 carbon atoms and most specifically up to 8 carbon atoms or hydrogen; r is an integer of from 1 to 4, more specifically 1 or 2 and most specifically 1; and a is 0, 1 or 2, more specifically 0 or 1 and most specifically 0.

A hydrolyzate of Formula (I) is where at least one $R^3$ is independently a hydrogen. A condensate is a polysiloxane formed from the reaction of at least two hydrolyzates of Formula (I), which are bonded together through a Si—O—Si bond.

Non-limiting examples of $R^1$ are methylene, ethylene, propylene, isopropylene, butylene, isobutylene, cyclohexylene and phenylene groups.

In one embodiment X is a functional group, such as the non-limiting examples of amino, mercapto, glycidoxy, epoxycyclohexyl, epoxycyclohexylethyl, hydroxyl, episulfide, acrylate, methacrylate, ureido, thioureido, vinyl, allyl, thiocarbamate, dithiocarbamate, ether, thioether, disulfide, trisulfide, tetrasulfide, pentasulfide, hexasulfide, xanthate, trithiocarbonate, dithiocarbonate, cyanurato, isocyanurato, —NHC(=O)OR$^5$ or —NHC(=O)SR$^5$ where $R^5$ is a monovalent hydrocarbyl group containing from 1 to 12 carbon atoms, more specifically from 1 to 8 carbon atoms or a —$R^1Si(R^2)_a(OR^3)_{3-a}$ group wherein each occurrence of $R^1$ is independently a linear, branched or cyclic divalent organic group of up to 12 carbon atoms, more specifically up to 10 carbon atoms, and most specifically from up to 8 carbon atoms and optionally containing one or more heteroatoms, such as the non-limiting examples of O, N, P, Cl, Br, I and S, with the proviso that —NHC(=O)O— or —NHC(=O)S— and the silicon atom of the silyl group are bonded to the $R^1$ group through a covalent bond to a carbon atom of $R^1$, thereby forming a bridge between organofunctional group X and the silyl group; each occurrence of $R^2$ is independently an alkyl, alkoxy-substituted alkyl, aryl, or aralkyl, each containing up to 16 carbon atoms, more specifically from up to 12 carbon atoms and most specifically from up to 8 carbon atoms, each $R^3$ is independently a hydrogen, acetyl, alkyl, or alkoxy-substituted alkyl, each containing up to 16 carbon atoms, more specifically up to 12 carbon atoms and most specifically up to 8 carbon atoms or hydrogen; and a is 0, 1 or 2, more specifically 0 or 1 and most specifically 0.

In one embodiment the set of univalent organofunctional groups herein includes, but is not limited to, —NH$_2$, —SH, —O—CH$_2$—C$_2$H$_3$O, —CH$_2$—CH$_2$—CH$_2$—C$_6$H$_9$O, —C$_6$H$_9$O, —NR(C=O)OR, —O(C=O)NRR, —NR(C=O)NR$_2$, (—N)(NR)(NR)C$_3$O$_3$, where (—N)(NR)NR)C$^3$O$^3$ represents a monovalent isocyanurate ring, C$_2$H$_3$O represents an oxirane, C$_6$H$_9$O represents 7-oxa-[4.1.0]cycloheptyl, each occurrence of R is independently selected from the group consisting of hydrogen, alkyl of from 1 to 6 carbon atoms, cycloalkyl of from 3 to 10 carbon atoms, alkenyl of from 2 to 6 carbon atoms, arylene of from 6 to 10 carbon atoms or alkarylene of from 7 to 12 carbon atoms.

In another embodiment herein the set of divalent organofunctional groups herein includes, but is not limited to, carbamate, —(—)N(C=O)OR, ureido —NR(C=O)NR—, and divalent isocyanurato, (—N)$_2$(NR)C$_3$O$_3$ where R is independently selected from the group of hydrogen, alkyl of from 1 to 6 carbon atoms, cycloalkyl of from 3 to 10 carbon atoms, alkenyl of from 2 to 6 carbon atoms, arylene of from 6 to 10 or alkarylene from 7 to 12 carbon atoms.

In yet another embodiment herein, the set of trivalent organofunctional groups herein includes, but is not limited to, carbamate, (—)$_2$NC(=O)O—, ureido, (—)$_2$NC(=O)NR—, and trivalent isocyanurato (—N)$_3$C$_3$O$_3$, wherein each occurrence of R is independently selected from the group consisting of hydrogen, alkyl of from 1 to 6 carbon atoms, cycloalkyl of from 3 to 10 carbon atoms, alkenyl of from 2 to 6 carbon atoms, arylene of 6 to 10 carbon atoms, or alkarylene of 7 to 12 carbon atoms.

In a further embodiment herein, the set of tetravalent organofunctional groups herein includes, but is not limited to ureido, (—)$_2$N(C=O)N(—)$_2$.

In a specific embodiment the organofunctional silane is univalent ureido —NR(C=O)NR$_2$, divalent ureido —NR(C=O)NR— and (—)$_2$N(C=O)NR$_2$, trivalent ureido (—)$_2$NC(=O)NR—, tetravalent ureido (—)$_2$N(C=O)N(—)$_2$ and trivalent isocyanurato (—N)$_3$C$_3$O$_3$ where R is independently selected from the group of hydrogen, alkyl of from 1 to 6 carbon atoms, cycloalkyl of from 3 to 10 carbon atoms, alkenyl of from 2 to 6 carbon atoms, arylene of from 6 to 10 or alkarylene from 7 to 12 carbon atoms.

In a specific embodiment r is an integer of from 1 to 4 and specifically from 2 to 4, and more specifically 3 to 4.

In one embodiment, the silane-containing coating solution contains ureido silanes having the general Formula (II):

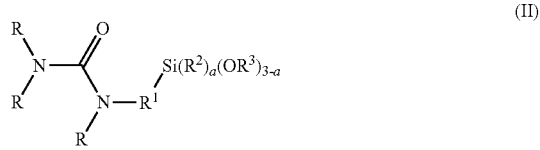

or condensates of such silane wherein each occurrence of R is independently selected from the group consisting of hydrogen, alkyl of from 1 to 6 carbon atoms, cycloalkyl of from 3 to 10 carbon atoms, alkenyl of from 2 to 6 carbon atoms, arylene of from 6 to 10 carbon atoms or alkarylene of from 7 to 12 carbon atoms, each occurrence of $R^1$ is independently a linear, branched or cyclic divalent organic group of up to 12 carbon atoms, more specifically up to 10 carbon atoms, and most specifically from up to 8 carbon atoms and optionally containing one or more heteroatoms, such as the non-limiting examples of O, N, P, Cl, Br, I and S; each occurrence of $R^2$ is independently an alkyl, alkoxy-substituted alkyl, aryl, or aralkyl, each containing up to 16 carbon atoms, more specifically from up to 12 carbon atoms and most specifically from up to 8 carbon atoms, each $R^3$ is independently a hydrogen, acetyl, alkyl, or alkoxy-substituted alkyl, each containing up to 16 carbon atoms, more specifically up to 12 carbon atoms and most specifically up to 8 carbon atoms or hydrogen; and a is 0, 1 or 2, more specifically 0 or 1 and most specifically 0.

A condensate of Formula (II) has the general Formula (III):

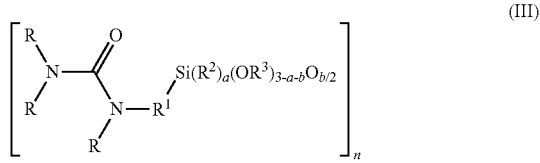

(III)

wherein each occurrence of R is independently selected from the group consisting of hydrogen, alkyl of from 1 to 6 carbon atoms, cycloalkyl of from 3 to 10 carbon atoms, alkenyl of from 2 to 6 carbon atoms, arylene of from 6 to 10 carbon atoms or alkarylene of from 7 to 12 carbon atoms, each occurrence of $R^1$ is independently a linear, branched or cyclic divalent organic group of up to 12 carbon atoms, more specifically up to 10 carbon atoms, and most specifically from up to 8 carbon atoms and optionally containing one or more heteroatoms, such as the non-limiting examples of O, N, P, Cl, Br, I and S; each occurrence of $R^2$ is independently an alkyl, alkoxy-substituted alkyl, aryl, or aralkyl, each containing up to 16 carbon atoms, more specifically from up to 12 carbon atoms and most specifically from up to 8 carbon atoms, each $R^3$ is independently a hydrogen, acetyl, alkyl, or alkoxy-substituted alkyl, each containing up to 16 carbon atoms, more specifically up to 12 carbon atoms and most specifically up to 8 carbon atoms or hydrogen; and each occurrence of a is independently 0, 1 or 2, more specifically 0 or 1 and most specifically 0; each occurrence of b is independently 1, 2 or 3, more specifically 2 or 3, with the proviso that a+b=3, and n is 2 to 25, more specifically 2 to 8 and most specifically 3 to 5.

Preferably, R is hydrogen, $R^1$ is methylene, ethylene or propylene and $R^3$ is individually chosen from the group consisting of hydrogen, ethyl, methyl, propyl, iso-propyl, butyl, iso-butyl, sec-butyl, and acetyl.

The particularly preferred ureido silane employed in the invention is γ-ureidopropyltrimethoxysilane having the general Formula (IV):

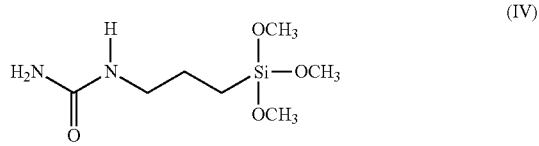

(IV)

This compound is commercially available under the designation "Silquest A-1524 silane" from Momentive Performance Materials. 3-Ureidopropyltriethoxysilane can also be used to prepare the hydrolyzates, in which at least one of the Si—OCH$_3$ group reacts with water to form a Si—OH group, or a condensate in which at least two hydrolyzates react with each other to form a polysiloxane. Pure 3-ureidopropyltriethoxysilane is a waxy solid material. A solvent may be used to dissolve the waxy solid. Commercially available 3-ureidopropyltriethoxysilane is dissolved in methanol, and as a result, it is not a pure compound but contains both methoxy and ethoxy groups attached to the same silicon atom. When fully hydrolyzed, the hydrolyzate is 3-ureidopropylsilanetriol.

In one embodiment herein the organofunctional silane used to prepare the silane-containing coating composition or the hydrolyzate or the condensate is selected from the group consisting of vinylmethyldiethoxysilane, vinyltrimethoxysilane, vinyldimethylethoxysilane, vinyltriethoxysilane, vinyltripropoxysilane, vinyl-tris(2-methoxyethoxysilane), styrylethyltrimethoxysilane, gamma-acryloxypropyltrimethoxysilane, gamma-(acryloxypropyl)methyldimethoxysilane, gamma-methacryloxypropyltrimethoxysilane, gamma-methacryloxypropyltriethoxysilane, gamma-methacryloxypropylmethyldimethoxysilane, gamma-methacryloxypropylmethyldiethoxysilane, gamma-methacryloxypropyl-tris-(2-methoxyethoxy)silane, beta-(3,4-epoxycyclohexyl)ethyltrimethoxysilane, beta-(3,4-epoxycyclohexyl)ethyltriethoxysilane, gamma-glycidoxypropyltrimethoxysilane, gamma-glycidoxypropyltriethoxysilane, gamma-glycidoxypropylmethyldiethoxysilane, gamma-glycidoxypropylmethyldimethoxysilane, gamma-mercaptopropyltrimethoxysilane, gamma-mercaptopropyltriethoxysilane, gamma-thiooctanoylpropyltrimethoxysilane, gamma-thiooctanoylpropyltriethoxysilane, bis-(trimethoxysilylpropyl)tetrasulfane, bis-(triethoxysilylpropyl)disulfane, gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane, gamma-carbamatopropyltrimethoxysilane, gamma-carbamatopropyltriethoxysilane, isocyanurate propyltrimethoxysilane, bis-(trimethoxysilylpropyl)urea, bis-(triethoxysilylpropyl)urea, 2-cyanoethyltrimethoxysilane, 2-cyanoethyltriethoxysilane and combinations thereof.

In one specific embodiment the organofunctional silane used to prepare the silane-containing coating composition, or the hydrolyzate or the condensate is selected from the group consisting of gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane, N,N'-bis-(3-triethoxysilylpropyl)urea, N,N'-bis-(3-trimethoxysilylpropyl)urea, N,N'-bis-(3-diethoxymethylsilylpropyl)urea, N,N'-bis-(3-diisopropoxymethylsilylpropyl)urea, N,N-bis-(3-triethoxysilylpropyl)urea, N,N-bis-(3-trimethoxysilylpropyl)urea, N,N-bis-(3-diethoxymethylsilylpropyl)urea, N,N-bis-(3-diisopropoxymethylsilylpropyl)urea, N,N,N'-tris-(3-triethoxysilylpropyl)urea, N,N,N'-tris-(3-trimethoxysilylpropyl)urea, N,N,N'-tris-(3-diethoxymethylsilylpropyl)urea, N,N,N'-tris-(3-diisopropoxysilylpropyl)urea, N,N,N',N'-tetrakis-(3-triethoxysilylpropyl)urea, N,N,N',N'-tetrakis-(3- trimethoxysilylpropyl)urea, N,N,N,'N'-tetrakis-(3-diethoxymethylsilylpropyl)urea, N,N,N,'N'-tetrakis-(3-diisopropoxymethylsilylpropyl)urea, tris-(3-trimethoxysilylpropyl)isocyanurate, and combinations thereof.

In one specific embodiment the organofunctional silane used to prepare the silane-containing coating solution, or the hydrolyzate or the condensate is selected from the group consisting of gamma-ureidopropyltrimethoxysilane, gamma-ureidopropyltriethoxysilane, gamma-ureidopropyldimethoxyethoxysilane, gamma-ureidopropylmethoxydiethoxysilane, gamma-ureidopropylmethyldimethoxysilane, gamma-ureidopropylmethyldiethoxysilane, gamma-ureidopropylmethylmethoxyethoxysilane and combinations thereof.

In one other embodiment herein a silane-containing coating composition which contains at least one organofunctional silane, hydrolyzate or condensate, has hazardous air pollutants (HAPs) at a level of HAPs of specifically less than 1 weight percent, more specifically less than 0.2 weight percent, even more specifically less than 0.05 weight percent and most specifically less than 0.01 weight percent, said weight percents being based on the total weight of the composition.

The removal of HAP can be accomplished through sparging with an inert gas such as the non-limiting example of nitrogen. In one more specific embodiment such sparging can be conducted for a period of from 2 to 96 hours, more specifically of from 4 to 72 hours, even more specifically of from 6 to 48 hours and most specifically of from 8 to 24 hours. In another embodiment herein some other techniques that can be used herein for the removal of HAP are reduced pressure and/or distillation.

In one specific embodiment herein HAPs are any compounds used in paints that have been identified as HAPs in the Clean Air Act Amendments of 1990 of the United States of America. In one specific embodiment HAPs can be byproducts formed from the hydrolysis of organofunctional silane (a) described above. In one specific embodiment HAPs includes acetamide, acrylamide, acrylic acid, acrylonitrile, allyl chloride, aniline, benzene, 1,3-butadiene, caprolactam, catechol, cumene, 1,2-dichloroethane, dichloroethyl ether, diethanolamine, dimethylamino-azobenzene, dimethylfomamide, dimethylphthalate, epichlorohydrin, ethyl acrylate, ethyl benzene, ethylene dibromide, ethylenimine, formaldehyde, hexachlorobenzene, n-hexane, hydroquinone, isophorone, maleic anhydride, methanol, methyl ethyl ketone, methyl isobutyl ketone, methylene chloride, naphthalene, nitrobenzene, 2-nitropropane, pentachlorophenol, phenol, propylene oxide, styrene, 1,1,2,2-tetrachloroethane, toluene, 2,4-toluene diisocyanate, 1,1,1-trichloroethane, trichloroethylene, 2,4,6-trichlorophenol, vinyl acetate, vinyl chloride, xylenes, m-xylene, o-xylene, p-xylene and combinations thereof. An example is the release of methanol from the hydrolysis of gamma-ureidopropyltrimethoxysilane.

The amount of HAPs in the composition is determined by a gas chromatographic method in which a weighed amount of an internal standard is added to a weighed amount of composition to quantify the amount of HAPs. The identity of the HAPs in the composition is determined from the retention times of the HAPs components, which were determined using pure HAPs standards. The response factor for each HAPs component was determined by gas chromatographic method using a weighed sample of the pure HAPs standard and a weighed sample of the internal standard. The internal standard is an organic compound which has a retention time different than the HAPs, organofunctional silane, hydrolyzate and/or condensate which are present in the composition and is soluble in the composition.

In another specific embodiment a silane-containing coating composition, which contains at least one organofunctional silane, hydrolyzate or condensate, has levels of HAPs of specifically less than 1 weight percent, more specifically less than 0.2 weight percent, even more specifically less than 0.05 weight percent and most specifically less than 0.01 weight percent, said weight percents being based on the total weight of the composition, and is low in volatile organic compound (VOC). VOC is any organic compound which participates in any atmospheric photochemical reactions; that is any organic compound other than those, which the Environmental Protection Agency of the United States of America (EPA) designates as having negligible photochemical reactivity. In a more specific embodiment VOC can be selected from the group consisting of methanol, ethanol, n-propanol, 2-propanol, n-butanol, 2-butanol, tert-butanol and combinations thereof. In a further embodiment herein, low in VOC is a level of VOC of specifically less than 10 weight percent, more specifically less than 5 weight percent, even more specifically less than 2 weight percent and most specifically less than 1 weight percent, said weight percents being based on the total weight of the composition.

In the application of coatings, such as in the application of coatings to metal surfaces, VOC is calculated according EPA Method 24 from percent non-volatile, with corrections on exempt solvents and water. The non-volatile content is measured based on ASTM Standards D2369 and D3960. In one embodiment, a weighed sample of material is placed in a dish and placed in a convection oven at 110° C. for 1 hour. The weight remaining in the dish is then determined. The VOC is determined by subtracting the weight remaining in the dish from the weighed sample and then dividing the difference by the weighed sample. The percent VOC is determined by multiplying the quotient by 100%.

In one embodiment, the silane-containing coating composition further contains a colloidal oxide-containing sol such as a metal oxide sol or a silica sol. In certain embodiment, the sols preferably include either silica and/or cerium oxide particles. In a preferred aspect of the invention, stabilizing agents is/are added to the silane-containing coating composition to enhance product stability and shelf life.

The silica sol material comprises aqueous colloidal silica preferably with acidic pH. Exemplary silica sol materials may be purchased from Cabot Corporation and from other suppliers such as Wacker Chemie, Degussa, Nissan Chemical, and Nalco Chemical Company. An example of an effective silica sol, Cab-O-Sperse A205, is an aqueous dispersion of high purity fumed silica in a deionized water. This sol has a pH of about 5-7 and a solids content of about 12%. The viscosity is <100 cPs and the specific gravity is about 1.07.

Exemplary cerium oxide sols are also commercially available. Generally, these comprise cerium oxide particles in aqueous colloidal suspension. Commercially available cerium oxide sols that may be mentioned as exemplary include colloidal cerium oxide nitrate and cerium oxide acetate, both available from Rhodia and those available from Nyacol Nano Technologies Inc. The preferred cerium oxide acetate sol includes about 20% cerium oxide particles. Exemplary Cerium oxide sols include those having particle sizes of less than about 100 nm. Exemplary pHs are on the order of about 1-9. Other metal oxide sols such as ZnO, $ZrO_2$, $TiO_2$ and $Al_2O_3$ may also be mentioned.

In still another embodiment, the silane-containing coating composition further comprises a stabilizing agent. A host of stabilizing agents may be mentioned as exemplary. For example, alcohols, glycols, triols, polyols, glycol ethers, esters, ketones, pyrrolidones, and polyethersilanes are exemplary. Specific stabilizers include: ethanol, 1-propanol, 2-propanol (i-propanol), 2-methyl-1-propanol (i-butanol), 2-methyl-2-propanol (tert-butanol), 1-butanol, 2-butanol, 2-methyl-1-butanol, 2-methyl-2-butanol, 2,2-dimethyl-1-propanol, 1-pentanol, 2-pentanol, 4-methyl-2-pentanol; glycols including: propylene glycol, 1,3-butanediol, 1,4-butane diol, 2-methyl-1,3-propanediol, 2-methyl-2,4-pentanediol (hexylene glycol), diethylene glycol, triethylene glycol, tetraethylene glycol, poly(ethylene glycol), dipropylene glycol, tripropylene glycol, poly(propylene glycol), 1,5-pentanediol, esterdiol 204, 2,2,4-trimethylpentanediol, 2-ethyl-1,3-hexanediol, glycerol, glycerol ethoxylate, glycerol ethoxylate-co-propoxylate triol, glycerol propoxylate, pentaerythritol, glycol ethers such as 1-methoxy-2-propanol (propylene glycol methyl ether), 1-ethoxy-2-propanol, 1-propoxy-2-propanol, 1-butoxy-2-propanol, 2-methoxyethanol, 2-ethoxyethanol, 2-propoxyethanol, 2-butoxyethanol, 2-(2-methoxyethoxyl)ethanol, 2-(2-ethoxyethoxy)ethanol, 2-(2-propoxyethoxy)ethanol, 2-(2-butoxyethoxy) ethanol (butyl carbitol), di(propylene glycol)butyl ether, methoxytriglycol (tri(ethylene glycol)monomethyl ether), ethoxytriglycol (tri(ethylene glycol)monoethyl ether), butoxytriglycol (tri(ethylene glycol)monobutyl ether, methoxypolyethylene glycol (poly(ethylene glycol)methyl ether), poly(ethylene glycol)butyl ether, poly(ethylene glycol)dimethylether, poly(ethylene glycol-co-propylene glycol), poly(ethylene glycol-co-propylene glycol)monobutyl ether, poly(propylene glycol)monobutyl ether, di(propylene glycol)dimethylether; esters including methyl acetate, ethyl acetate, ethyl lactate, 2-methoxyethyl acetate, 2-ethoxyethyl acetate, 2-butoxyethyl acetate, 2-(2-methoxyethoxyl)ethyl acetate, 2-(2-ethoxyethoxy)ethyl acetate, 2-(2-butoxyethoxy)ethyl acetate, glycol diacetate, triethylene glycol diacetate, propylene glycol methyl ether acetate(1-methoxy-2-propanol acetate), propylene glycol ethyl ether acetate, and ketones including acetone, methyl ethyl ketone, 2,4-pentane dione, diacetone alcohol and polyether silanes including Silquest A-1230.

Additionally, $C_1$-$C_4$ alkoxylated silane compounds may be included as an optional adjuvant to the silane-containing coating solution to provide additional Si—O bonds. These adjuvant compounds can be represented by the Formula (V)

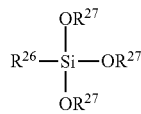
(V)

wherein $R^{26}$ is a monovalent hydrocarbon group having from 1 to 10 carbon atoms or $OR^{27}$ and each $R^{27}$ is independently chosen from $C_1$-$C_4$ alkyl. Specific examples include tetraethylorthosilicate (TEOS) and methyltriethoxysilane. These adjuvant compounds will hydrolyze in solution to provide a source of Si—O bonds.

In another embodiment, the silane-containing coating composition comprises:
(a) 0.01 to 80 weight percent ureido silane and/or hydrolyzate forms thereof;
(b) 0.001 to 36 weight percent colloidal metal oxide and/or silica sol particles; and,
(c) optional stabilization additive percent in an amount of up to 25 weight percent, and
(d) optional alkoxylated silane compound and/or hydrolyzate thereof in an amount of up to 25 weight percent:
(e) optional pH adjustment agents in an amount of up to 2 weight percent; and
(f) remainder being water,
wherein the weight percents are based on the total weight of the silane-containing coating composition. The weight of the composition is, in total, 100 weight percent. The pH of the sol compositions may preferably range from 1 to 7, more specifically, from 3 to 6.5.

In another embodiment, the silane-containing coating compositions have the following range (in weight percent) of the components:
(a') 3 to 60 weight percent ureido silane and/or hydrolyzate form thereof;
(b') 0.001 to 10 wt %/o Si and/or Ce oxide particles;
(c') 1 to 15 weight percent stabilizing agent;
(d') 1-15 weight percent adjuvant;
(e') Up to 2 wt % pH regulating agents; and
(f') remainder being water, wherein the weight percents are based on the total weight of the silane-containing coating composition.

In one embodiment, the silane-containing coating solution further contains a water soluble organic dye (e) that will not interfere with the coating composition. In particular, water soluble organic dye (e) will not form precipitates or result in gelation of the suspension at 25° C. temperature for a period of at least 48 hours, more specifically, for a period of 48 hours to at least 18 months. In one embodiment, water soluble organic dye (e) will not result in destabilization of the colloidal metal oxide aqueous colloidal suspension, especially cerium oxide aqueous colloidal suspension. In one embodiment, water soluble organic dye (e) is such that it has an acetate counterion. In another embodiment herein, water soluble organic dye (e) is stable, which means that the dye will not form precipitates or result in gelation of the suspension at 25° C. temperature for a period of at least 48 hours, more specifically, for a period of 48 hours to at least 18 months.

In one specific embodiment, water soluble organic dye (e) has a positive charge and counterion derived from a carboxylic acid containing from 1 to 6 carbon atoms, more specifically from 1 to 3 carbon atoms, such as the non-limiting examples of formic acid, acetic acid and the like.

In one non-limiting embodiment, water soluble organic dye (e) has the general Formula (VI):

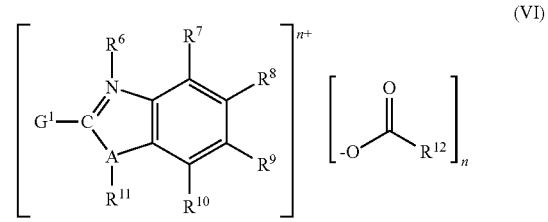

wherein:
$G^1$ is an organic group having from 1 to 20 carbon atoms and containing at least one oxygen or nitrogen heteroatom;

A is a nitrogen atom or (—)₃C—R*, where R* is a monovalent group chosen from alkyl, cycloalkyl, alkenyl, aralkyl or aryl group having up to 10 carbon atoms;

$R^6$ is an alkyl, a hydroxylalkyl, an alkoxyalkyl, a cycloalkyl, an aralkyl optionally substituted with a halogen or alkoxy group, an aryl optionally substituted with a halogen or alkoxy group, a cyanoalkyl, a carbamatoalkyl or a carboalkoxyalkyl group containing up to 10 carbon atoms, or hydrogen;

$R^7$ is an alkyl, alkoxy, aryl alkylsulfonyl, or arylsulfonyl group containing up to 10 carbon atoms or hydrogen;

$R^8$ is an alkyl, alkoxy, aryl alkylsulfonyl, arylsulfonyl, or aminosulfonyl group containing up to 10 carbon atoms or hydrogen;

$R^9$ is an alkyl, alkoxy, aryl alkylsulfonyl, or arylsulfonyl group containing up to 10 carbon atoms or hydrogen;

$R^{10}$ is an alkyl, alkoxy, aryl alkylsulfonyl, or arylsulfonyl group containing up to 10 carbon atoms or hydrogen;

$R^{11}$ is an alkyl, a hydroxylalkyl, an alkoxyalkyl, cycloalkyl, an aralkyl optionally substituted with a halogen or alkoxy group, an aryl optionally substituted with a halogen or alkoxy group, a cyanoalkyl, a carbamatoalkyl or an alkoxycarbonylalkyl group containing up to 10 carbon atoms or hydrogen;

$R^{12}$ is an alkyl group containing from 1 to 6 carbon atoms or hydrogen; and n is an integer of from 1 to 3, more specifically 1 or 2, and most specifically 1.

In one embodiment, $G^1$ is a monovalent organic group of the general Formula (VII):

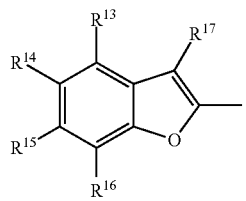

(VII)

wherein:

$R^{13}$ is an alkyl or alkoxy group containing from 1 to 6 carbon atoms, halogen, hydrogen or together with $R^{14}$ forms a fused aryl group containing up to 16 carbon atoms, or a ring containing a —O—CH₂—O— group or —O—CH₂CH₂—O— group bonded to the aromatic ring of the structure (VII) which contains up to 16 carbon atoms;

$R^{14}$ is an alkyl or alkoxy group containing from 1 to 6 carbon atoms, hydrogen, halogen, carboxyl, carboalkoxy, aminocarbonyl, carbamato, sulfonyl, alkylsulfonyl, aminosulfonyl or together with $R^{13}$ or $R^{15}$ forms a fused aryl group containing up to about 16 carbon atoms, or a ring containing a —O—CH₂—O— group or —O—CH₂CH₂—O— group bonded to the aromatic ring of the structure (V) which contains up to 16 carbon atoms;

$R^{15}$ is an alkyl or alkoxy group of from 1 to about 6 carbon atoms, a halogen or a hydrogen or together with $R^{14}$ or $R^{16}$ forms a fused aryl group containing up to about 16 carbon atoms, or together with $R^{14}$ or $R^{16}$ forms a fused ring containing a —O—CH₂—O— group or —O—CH₂CH₂—O— group bonded to the aromatic ring of the structure (V) which contains up to about 16 carbon atoms, or a monovalent group of from 2 to about 12 carbon atoms derived from 2H-[1,2,3]triazole;

$R^{16}$ is an alkyl or alkoxy group of from 1 to about 6 carbon atoms, a halogen or hydrogen or together with $R^{15}$ forms a fused aryl group containing up to 16 carbon atoms, or a ring containing a —O—CH₂—O— group or —O—CH₂CH₂—O— group bonded to the aromatic ring of the structure (V) which contains up to about 16 carbon atoms; and $R^{17}$ is an alkyl group of from 1 to about 6 carbon atoms, hydrogen, or a phenyl group which is optionally substituted with an alkyl or alkoxy group of up to about 8 carbon atoms.

In another embodiment, $G^1$ is a monovalent organic group of the general Formula (VIII):

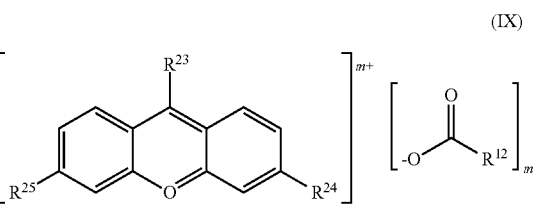

(VIII)

wherein:

each $R^{18}$, $R^{19}$, $R^{20}$, $R^{21}$ and $R^{22}$ is independently an alkyl group of from 1 to 6 carbon atoms or hydrogen.

In another non-limiting embodiment, the water soluble organic dye (e) has the general Formula (IX):

(IX)

wherein:

$R^{12}$ is an alkyl group containing from 1 to 6 carbon atoms or hydrogen;

$R^{23}$ is hydrogen, an alkyl group of from 1 to 6 carbon atoms, an aryl group of from 6 to 10 carbon atoms, an aralkyl group of from 7 to 12 carbon atoms or an aryl group of from 6 to 12 carbon atoms substituted with a hydroxycarbonyl group (—C(=O)OH) or an alkoxycarbonyl group (—C(=O)OR²⁶), where $R^{26}$ is an alkyl group of from 1 to 4 carbon atoms;

$R^{24}$ is hydrogen, an alkyl group containing 1 to 6 carbon atoms, hydroxyl or amino having the structure —NR²⁷R²⁸, where $R^{27}$ and $R^{28}$ are each independently a hydrogen or alkyl group of from 1 to 6 carbon atoms;

$R^{25}$ is hydrogen, an alkyl group containing 1 to 6 carbon atoms, hydroxyl or amino having the structure —$NR^{27}R^{28}$, where $R^{27}$ and $R^{28}$ are each independently a hydrogen or alkyl group of from 1 to 6 carbon atoms; and m is an integer from 1 to 3, more specially 1 or 2, and most specifically 1.

In one further embodiment herein the water soluble organic dye is derived from xanthenylium, 1H-benzoimidazole, 3H-indole, 2-allylidene-2,3-dihydro-1H-indole and/or benzofuran.

The water soluble organic dye used herein can be selected from the group consisting of Amezine Rhodamine B Liquid, Amezine Brilliant R Red P Liquid, Amewhite BAC Liquid and combinations thereof.

The water soluble organic dye used herein can be a fluorescing dye or merely a visible dye. It will be understood that a fluorescing dye may still be visible to the naked eye, but a visible dye will be such that it does not contain fluorescing components.

If the water soluble organic dye is a visible dye, it is such that it may have a characteristic color under visible light which is visibly detectable by eye in a coating of the desired thickness on a substrate. This would allow a qualitative determination of whether the coating is present on the substrate along with the ability to quantify the thickness of the coating according to the methods of the invention herein.

If the water soluble organic dye is a fluorescing dye, it will be such that it produces a detectable fluorescence even when small amounts of the dye are used in the stable suspension or where the stable suspension (the coating composition) is very thin. The wavelength of light which causes the dye to fluoresce should be different from the wavelength of light emitted from the dye when it fluoresces. This ensures that there is no undue interference with the measurement of the intensity of the fluorescence by the light used to cause the dye to fluoresce.

In one embodiment the stable suspension can further comprise water, specifically deionized water.

In one embodiment, the substrate is selected from the group consisting of cold rolled steel, hot dip galvanized steel, electrogalvanized steel, aluminum, magnesium, zinc alloy, zinc coated steel and other metals.

In one specific embodiment, the method for determining the weight of the passivation coating composition on the surface of a metal substrate comprises:
(i) preparing a series of passivation coating compositions with different concentrations of at least one of component(s) (a)-(f) above;
(ii) coating the same or different metal substrates with each of the foregoing passivation coating compositions;
(iii) optionally, drying the passivation coating compositions as applied to each metal substrate under the same drying conditions that are used in any known or conventional on-line coating procedure;
(iv) determining the amount of passivation coating composition on the surface of each coated metal substrate and the area that is coated by the composition, the amount of passivation coating composition being determined gravimetrically using the equation, weight of passivation coating composition=$(w^2-w^1)$/(area of coated surface) if only one side of the substrate is coated, or weight of passivation coating composition=$(w^2-w^1)$/(2)(area of coated surface) if two sides of the substrate are coated;

or the amount of passivation coating composition being determined by using the XRF method where the XRF standard calibration curve is used to develop a least squared linear regression equation;
(v) acquiring an FTIR spectrum for each passivation-coated substrate of known passivation composition weight and integrating the peaks associated with a particular functional group to yield an integral of the absorbances;
(vi) plotting the passivation coating composition weight versus the integral of the absorbances and calculating the least squares linear regression equation;
(vii) measuring the passivation coating composition weight on-line by obtaining the FTIR spectrum and integrating the spectrum associated with the functional group to yield an integral of the absorbances;
(viii) using the equation of step (vi) to calculate the weight of the passivation coating composition on the metal substrate.

The passivation coating composition may be applied to the surface of the substrate by any known or conventional application technique such as spraying, immersion or roll coating in a batch or continuous operation. The temperature of the passivation coating composition at application is typically from 10° C. to 85° C., and preferably from 15° C. to 60° C.

Continuous operations are typically used in the coil coating industry and also for mill application. In the coil industry, the substrate is cleaned and rinsed and then usually contacted with the coating solution by roll coating with a chemical coater. The coated strip is then dried by heating and painted and baked by known or conventional coil coating processes. Mill application of the coating composition solution can be by immersion, spray or roll coating applied to one or both surface of the freshly manufactured metal substrate. Excess passivation coating composition is typically removed by wringer rolls. After the passivation coating composition has been applied to the metal surface, the metal is dried at room temperature or at elevated temperatures to remove the water and promote the condensation reactions of the components with themselves and with the surface to form the dried and cured passivation coating composition on the surface of the substrate. Alternately, the coated metal substrate can be heated at from 65° C. to 125° C. for 2 to about 60 seconds to produce a coated substrate having a dried residue of the passivation coating composition. If the substrate is already heated from the hot melt production process, no post-application of heating to the coated substrate is required to facilitate drying. The temperature and time for drying the passivation coating composition will depend upon the characteristics of the passivation coating composition and type of substrate.

Before depositing the passivation coating compositions upon a surface of the selected metal substrate, foreign matter is typically removed from the metal surface by thoroughly cleaning and degreasing the surface. The surface can be cleaned by physical means, such as by mechanical abrasion, or by chemical means, such as by cleaning or degreasing the surface with commercially available alkaline or acidic cleaning agents, such as sodium metasilicate and sodium hydroxide. A non-limiting example of a cleaning agent is CHEMKEEN 163, a phosphate cleaner, which is commercially available from PPG Industries, Inc. of Pittsburgh, Pa. Following the cleaning step, the metal substrate is usually rinsed with water, specifically deionized water, in order to remove any residue. The metal substrate can be air dried using an air knife, by flashing off the water by brief exposure of the substrate to a high temperature, or by passing the substrate between squeegee rolls.

In yet another specific embodiment herein, the passivation coating composition described herein is applied to the metal surface to result in a weight of passivation coating composition of greater than or equal to 0.5 milligram per square foot (5 milligrams per square meter) of the coated surface, more specifically applied to the coated metal surface with a weight of passivation coating composition of from 0.5 to 500 milligrams per square foot (5.4 to 5,400 milligrams per square meter) being more specific weight of from 3 to 300 milligrams per square foot (32 to 3,200 milligrams per square meter).

After the passivation coating composition is applied on the substrate, the coating can be dried and/or cured at room temperature or by exposure to heat, using methods known by those skilled in the art.

The calibration standard is produced with one or more calibration samples having a predetermined weight of passivation coating composition on a substrate, representative of the range of the weights of passivation coating composition that are desirable. It is preferred that a more statistically significant calibration standard having eight calibration samples is utilized, including two calibration samples of blank substrate, two calibration samples representative of target weight of passivation coating composition, two calibration samples representative of low weight of passivation coating composition and two calibration samples representative of high weight of passivation coating composition. These calibration samples may be prepared using coating methods known to one skilled in the art.

The FTIR energy spectrum can be measured by a grazing angle head or an attenuated total reflection head. In one embodiment, the grazing angle is in the range of from 5 to 89 degrees, more specifically of from 60 to 89 degrees, and most specifically of from 75 to 89 degrees. In certain embodiment, the distance between the grazing angle head and the substrate is in the in the range of from 0 to 5 cm, more specifically of from 0 to 2.5 cm, and most specifically of from 0 to 1 cm.

The FTIR energy spectrum can be measured by a handheld spectrometer or a free standing spectrometer. Examples for the commercially available FTIR spectrometer include Agilent's 4100 ExoScan.

In still another embodiment, the integral of the FTIR spectrum is obtained by integrating the IR peaks between 1220.3 to 818.5 $cm^{-1}$, using a grazing angle head or an attenuated total reflection head, where the grazing angle is in the range of from 5 to 89 degrees, more specifically of from 60 to 89 degrees, and most specifically of from 75 to 89 degrees, the distance between the grazing angle head and the substrate is in the in the range of from 0 to 5 cm, more specifically of from 0 to 2.5 cm, and most specifically of from 0 to 1 cm.

The method of the present invention is particularly useful when the substrate having the passivation coating composition is a moving coil line. The measurement of the amount of dried passivation coating composition on the surface of the metal substrate is made on either a moving coil line or a coil line that is stop for a predetermined amount of an acquisition time during the weight measurement. An acquisition time that is too long, which is longer than 30 seconds might give rise to loss in productivity in the coil line. The acquisition time of the present invention is less than 30 seconds, more specifically less than 5 seconds, and most specifically less than one second.

The method of the present invention is particularly suitable for measuring the weight of the passivation coating composition in the range of from 0 to greater than 500 milligrams per square meter, more specifically of from 10 to greater than 500 milligrams per square meter, and most specifically of from 20 to greater than 500 milligrams per square meter ($mg/m^2$). It is noted that the substrate having the passivation coating composition should be substantially dried before the FTIR measurement.

Various features of the invention are illustrated by the examples presented below.

EXAMPLES

Preparation of Calibration Standards 1-10 for Silane-Containing Passivation Coating Composition Five passivation coating compositions were prepared by mixing distilled water with 23 weight percent colloidal ceria acetate in water. The mixture was stirred for 2 minutes, and then 3-ureidopropyltrimethoxysilane was added with adequate stirring for at least 15 minutes at ambient temperature to ensure adequate hydrolysis of the silane. The resulting silane bath solution was clear and colorless and kept at ambient temperature during the coating process. The amounts of 23 weight percent colloidal ceria acetate in water, 3-ureidopropyltrimethoxysilane and water are recorded in Tables 1 and 2.

Two types of metal substrates were selected for treating with the silane bath solutions. The substrates were cold rolled steel (CRS) and hot dip galvanized steel (HDG). CRS and HDG panels were obtained from ACT Laboratories. The metal substrates were cleaned by dipping in a pH 12, standard alkaline cleaning solution and rinsed with demineralized water until a water break free surface was obtained. The metal substrates were dried at room temperature.

The metal substrates were weighed using an analytical balance, where the weight was recorded as $w^1$, immersed in the silane bath solution for 5 seconds, dried at 100° C. for 10 minutes and then reweighed, where the weight was recorded as $w^2$. The amount of dried silane-containing coating on the surface was calculated by subtracting $w^1$ from $w^2$, and then dividing the difference by 2 times the surface area of the metal plates that were coated. The weights were divided by 2 to take into account that both sides of the metal substrate contained the dried silane film. The amount of dried silane-containing coating is then reported as milligrams per meter squared ($mg/m^2$). The amounts are recorded in Tables 1 and 2.

XRF was used to detect and analyze silicon on CRS and HDG substrates, by isolating the Si peak. The instrument used in the analysis was an X-Ray Fluorescence (XRF) instrument, Oxford Twin X using a Focus-5+ detector, available from Oxford Instruments. The instrument settings were a tube current of 750 μA, a voltage of 4 kV, a peak integration from 1.35 to 2.12 keV, and an accumulation time of 60 seconds. The reported intensities, reported as cps, were the average of five measurements. The results of the reading are recorded in Tables 1 and 2.

A standard calibration curve using the XRF method for each metal substrate was constructed by plotting the the amount of dried silane-containing coating ($mg/m^2$) versus the integrals of the signal (cps) calculating the least squared linear regression. The linear equation for CRS and HGD are:

Amount of dried silane-containing coating (mg/m$^2$)
=0.202×(integral, cps)+30.61 (for the CRS substrate); and Amount of dried silane-containing coating (mg/m$^2$)
=0.211×(integral, cps)−204.9 (for the HDG substrate).

TABLE 1

Data Used to Calculate the Standard Calibration Curve Using XRF Methodology on CRS Substrate.

| Amount of 3-ureido-propyltrimethoxysilane, weight percent | Amount of 23 weight percent colloidal ceria acetate, weight percent | Water weight percent | Amount of film, mg per m$^2$ | XRF integral, cps |
|---|---|---|---|---|
| 0.00 | 0.00 | 100.00 | 0 | 492.5 |
| 0.00 | 0.00 | 100.00 | 0 | 350.2 |
| 0.38 | 0.13 | 99.50 | 190 | 989.3 |
| 0.75 | 0.25 | 99.00 | 446 | 1482.8 |
| 0.75 | 0.25 | 99.00 | 356 | 1316.6 |
| 1.50 | 0.50 | 98.00 | 601 | 2600.5 |
| 1.50 | 0.50 | 98.00 | 606 | 2320.9 |
| 1.50 | 0.50 | 98.00 | 581 | 2533.9 |
| 4.50 | 1.50 | 94.00 | 1113 | 5856.5 |

TABLE 2

Data Used to Calculate the Standard Calibration Curve Using XRF Methodology on HDG Substrate.

| Amount of 3-ureido-proyltrimethoxysilane, weight percent | Amount of 23 weight percent colloidal ceria acetate, weight percent | Water weight percent | Amount of film, mg per m$^2$ | XRF integral, cps |
|---|---|---|---|---|
| 0.00 | 0.00 | 100.00 | 0 | 1345.3 |
| 0.00 | 0.00 | 100.00 | 0 | 1394.1 |
| 0.38 | 0.13 | 99.50 | 232 | 1920.9 |
| 0.38 | 0.13 | 99.50 | 232 | 2212.8 |
| 0.75 | 0.25 | 99.00 | 394 | 2268.8 |
| 0.75 | 0.25 | 99.00 | 394 | 2449.8 |
| 0.75 | 0.25 | 99.00 | 394 | 2706.7 |
| 0.75 | 0.25 | 99.00 | 394 | 3166.8 |
| 1.50 | 0.50 | 98.00 | 579 | 3399.3 |
| 1.50 | 0.50 | 98.00 | 579 | 3410.2 |
| 1.50 | 0.50 | 98.00 | 579 | 4275.6 |
| 1.50 | 0.50 | 98.00 | 579 | 4374.9 |
| 3.00 | 1.00 | 96.00 | 732 | 4152.4 |
| 4.50 | 1.50 | 94.00 | 1598 | 7628.3 |
| 4.50 | 1.50 | 94.00 | 1598 | 9160.9 |

A new set of calibration standards were made according to the above method on CRS and HDG substrates, except that the amount of the silane-containing bath had different concentrations. The amounts of the dried silane containing coatings were determined using the XRF method, and are reported in milligrams per meter squared. The dried silane-containing coatings were then analyzed using a 4100 ExoScan FTIR Grazing Angle Reflectance. The instrument is available from Agilent. IR spectra in the region of that was integrated was between 1220.3 to 818.5 cm$^{-1}$. The distance between the detector and the substrate is less than 2 cm and the acquisition time is 1 second. The integral of the absorbance is reported in Tables 3 and 4. FIG. 1 illustrates the changes in the intensity (integral of the absorbances) as the concentrations are varied for standards 2-5. Peaks that appear in this region are related to Si—O bonds. In particular, the peaks in the 900 to 1000 cm$^{-1}$ region relate to absorbance of Si—OH and Si—O-metal, the peaks in the 1150 cm$^{-1}$ region relate to absorbance of Si—O—Si, and the peaks in the 1200 cm$^{-1}$ region relate to Si—O—CH$_3$. The absorbance areas (integrals) under these peaks were arrived at by using the software provided by Agilent for this instrument.

TABLE 3

Data Used to Calculate the Standard Calibration Curve Using FTIR Methodology on CRS Substrate.

| Standard # | Coating Composition (in Weight Percent) | | | | Amount of film, mg per m$^2$ | FTIR integral, Abs |
| | (a) 3-ureido-propyltri-methoxysilane | (b) colloidal ceria acetate | (a) + (b) | Water | | |
|---|---|---|---|---|---|---|
| 1 | 0 | 0 | 0 | 100.000 | 0 | 0.482 |
| 2 | 0.038 | 0.012 | 0.05 | 99.950 | 7.66 | 0.972 |
| 3 | 0.075 | 0.025 | 0.1 | 99.900 | 15.1 | 1.179 |
| 4 | 0.300 | 0.100 | 0.4 | 99.600 | 53.47 | 1.625 |
| 5 | 0.750 | 0.250 | 1 | 99.000 | 182.2 | 3.913 |

TABLE 4

Data Used to Calculate the Standard Calibration Curve Using FTIR Methodology on HDG Substrate.

| Standard # | Coating Composition (in Weight Percent) | | | | Amount of film, mg per m$^2$ | FTIR integral, Abs |
| | (a) 3-ureido-propyltri-methoxysilane | (b) colloidal ceria acetate | (a) + (b) | Water | | |
|---|---|---|---|---|---|---|
| 6 | 0 | 0 | 0 | 100.000 | 0 | 0.396 |
| 7 | 0.038 | 0.012 | 0.05 | 99.950 | 3.86 | 1.035 |
| 8 | 0.075 | 0.025 | 0.1 | 99.900 | 16.67 | 1.253 |
| 9 | 0.300 | 0.100 | 0.4 | 99.600 | 52.12 | 2.355 |
| 10 | 0.750 | 0.250 | 1 | 99.000 | 262.8 | 5.528 |

A standard calibration curve using the FTIR method for each metal substrate was constructed by plotting the amount of dried silane-containing coating (mg/m$^2$) versus the integrals of the signal (cps) and calculating the least squared linear regression. The linear equation for CRS and HGD are:

Amount of dried silane-containing coating (mg/m$^2$)
=56.20×(integral, Abs)−40.16 (for the CRS substrate); and Amount of dried silane-containing coating (mg/m$^2$)
=53.80×(integral, Abs)−46.60 (for the HDG substrate).

The equations from the standard calibrations curves are used to determine the concentration of the dried silane-containing coating on coated CRS or HDG substrates. New calibration curves would need to be changed if different silanes, oxides and/or substrates are used. The measurement are made on-line by briefly stopping the line for a pre-determined period of time or carrying out the measurements as the line is moving. The advantages of the FTIR method is that the measurement are taken on-line either with short acquisition times or continuously, while the XRF method requires small samples to be cut from the substrate is inserted into the instrument in an off-line process.

Preparation of Calibration Standards for Titanium Tetraethoxide-Containing Passivation Coating Composition Five coating compositions are prepared by mixing distilled water with 0.15% glacial acetic acid and titanium tetraethoxide. The mixture is stirred for 30 minutes. The resulting bath solution is clear and colorless and keeps at ambient temperature during the coating process.

Two types of metal substrates are selected for treating with the titania bath solutions. The substrates are CRS and HDG. CRS and HDG panels were obtained from ACT Laboratories. Aluminum alloy panels were obtained from Q-Lab Corporation. The metal substrates are cleaned by dipping in a pH 12, standard alkaline cleaning solution and rinsed with de-mineralized water until a water break free surface is obtained. The metal substrates are dried at room temperature.

The metal substrates are weighed using an analytical balance, where the weight is recorded as $w^1$, immersed in the titania bath solution for 5 seconds, dried at 100° C. for 10 minutes and then reweighed, where the weight is recorded as $w^2$. The amount of dried titania-containing coating on the surface is calculated by subtracting $w^1$ from $w^2$, and then dividing the difference by 2 times the surface area of the metal plates that are coated. The weights are divided by 2 to take into account that both sides of the metal substrate contained the dried titania film. The amount of dried titania-containing coating is then reported as milligrams per meter squared ($mg/m^2$).

The dried titania-containing coatings are then analyzed using a 4100 ExoScan FTIR Grazing Angle Reflectance. The instrument is available from Agilent. The distance between the detector and the substrate is less than 2 cm and the acquisition time is 1 second. The peaks in the 400-1000 $cm^{-1}$ region relate to stretching mode of Ti—O—Ti. The absorbance areas (integrals) under these peaks are arrived at by using the software provided by Agilent for this instrument.

Preparation of Calibration Standards for Zirconium Tetraethoxide Coating-Containing Passivation Coating Composition Five coating compositions are prepared by mixing distilled water with 0.15% glacial acetic acid with zirconium tetraethoxide. The mixture is stirred for 30 minutes. The resulting bath solution is clear and colorless and kept at ambient temperature during the coating process.

Two types of metal substrates are selected for treating with the Zr bath solutions. The substrates are CRS and HDG. CRS and HDG panels are obtained from ACT Laboratories. Aluminum alloy panels are obtained from Q-Lab Corporation. The metal substrates are cleaned by dipping in a pH 12, standard alkaline cleaning solution and rinsed with de-mineralized water until a water break free surface is obtained. The metal substrates are dried at room temperature.

The metal substrates are weighed using an analytical balance, where the weight is recorded as $w^1$, immersed in the zirconium bath solution for 5 seconds, dried at 100° C. for 10 minutes and then reweighed, where the weight is recorded as $w^2$. The amount of dried zirconium-containing coating on the surface is calculated by subtracting $w^1$ from $w^2$, and then dividing the difference by 2 times the surface area of the metal plates that are coated. The weights are divided by 2 to take into account that both sides of the metal substrate contained the dried zirconium film. The amount of dried zirconium-containing coating is then reported as milligrams per meter squared ($mg/m^2$).

The dried zirconia-containing coatings are then analyzed using a 4100 ExoScan FTIR Grazing Angle Reflectance. The instrument is available from Agilent. The distance between the detector and the substrate is less than 2 cm and the acquisition time is 1 second. The peaks in the 400-1000 $cm^{-1}$ region relate to stretching mode of Zr—O—Zr. The absorbance areas (integrals) under these peaks are arrived at by using the software provided by Agilent for this instrument.

Examples 1-3

Determination of the Weight of an Aqueous Passivation Coating Composition Containing Ureidosilane and Cerium Oxide on a Cold Rolled Steel (CRS) Substrate Three passivation coating compositions were prepared by mixing distilled water with 23 weight percent colloidal ceria acetate in water. The mixture was stirred for 2 minutes, and then 3-ureidopropyltrimethoxysilane was added with adequate stirring for at least 15 minutes at ambient temperature to ensure adequate hydrolysis of the silane. The resulting silane bath solution was clear and colorless and kept at ambient temperature during the coating process. The weight ratio of the ureidosilane to the 23 weight percent colloidal ceria acetate in water was 3.0 parts ureidosilane to 1 part of 23 weight percent colloidal ceria acetate in water. The concentration of the silane and cerium oxide were varied The metal substrates were cold rolled steel (CRS) panels, obtained from ACT Laboratories. The metal substrates were cleaned by dipping in a pH 12, standard alkaline cleaning solution and rinsed with de-mineralized water until a water break free surface was obtained. The metal substrates were dried at room temperature. The metal substrates were immersed in the aqueous coating (silane bath solution) for 5 seconds and then dried at 100° C. for 10 minutes.

The amounts of the dried silane containing coatings were determined using the XRF method, and are reported in milligrams per meter squared. The dried silane-containing coatings were then analyzed using a 4100 ExoScan FTIR Grazing Angle Reflectance. The instrument is available from Agilent. IR spectra in the region of that was integrated was between 1220.3 to 818.5 $cm^{-1}$. The distance between the detector and the substrate is less than 2 cm and the acquisition time is 1 second. The integral of the absorbance is reported in Table 5. Using these absorbances, the weight of the dried silane film was calculated using the equation:

Amount of dried silane-containing coating ($mg/m^2$) =56.20(integral, Abs)−40.16, which was obtain from the standard calibration plot. The amounts of dried silane film that were determined by XRF method were also reported. The data indicate that the FTIR method can be used to determine the amounts of dried silane film on the surface of CRS substrate and are in good agreement with the amounts determined by the XRF method.

TABLE 5

Determination of the Amount of Dried Silane Film on the Surface of CRS.

| Example | XRF Measured Coating Weight | FTIR Peak Area | FTIR Coating Weight based on equation from calibration curve |
|---|---|---|---|
| 1 | 57.44 | 1.7796 | 60.1 |
| 2 | 35.04 | 0.9966 | 15.3 |
| 3 | 291.69 | 6.359 | 321.8 |

These examples are to be construed as exemplary in nature only and are not intended in any way to limit the appended claims. It is contemplated that a person having ordinary skill in the art would be able to produce obvious variations of the subject matter and disclosures herein contained that would be by reason of such ordinary skill within the literal or equitable scope of the appended claims.

What is claimed is:

1. A method for measuring the passivation coating composition weight per unit area on a metal substrate comprising the steps of:
   (i) applying a passivation coating composition to a metal substrate to obtain a passivation coating composition on the metal substrate;
   (ii) measuring a Fourier Transform Infrared energy spectrum of the passivation coating composition on the metal substrate of step (i) by obtaining the FTIR spectrum and integrating the spectrum associated with at least one functional group to yield an integral of the absorbances;
   (iii) obtaining a calibration standard using a Fourier Transform Infrared energy spectrum for a series of calibration samples having different predetermined weights of the passivation coating composition on the metal substrates by
      (a) coating a series of metal substrates with different amounts of passivation coating composition to form calibration samples;
      (b) determining the amount of passivation coating composition on the surface of each calibration sample and the area that is coated on each calibration sample, the amount of passivation coating composition being determined gravimetrically;
      (c) calculating the passivation coating composition weight per unit area for each calibration sample of step (b);
      (d) acquiring an FTIR spectrum for each calibration sample of known passivation composition weight per unit area of step (c) and integrating the peaks associated with at least one functional group to yield an integral of the absorbances; and
      (e) plotting the passivation coating composition weight per unit area for each calibration sample of step (c) versus the integral of the absorbances for each calibration sample of step (d) to obtain calibration standard; and
   (iv) calculating the passivation coating composition weight per unit area on the metal substrate using the calibration standard of step (iii) and integral of absorbances from step (ii).

2. The method of claim 1 wherein the FTIR energy spectrum is measured by a grazing angle head.

3. The method of claim 2 wherein the grazing angle is in the range of from 5 to 89 degrees.

4. The method of claim 2 wherein the distance between the grazing angle head and the substrate is in the range of from 0 to 5 cm.

5. The method of claim 1 wherein the FTIR energy spectrum is measured by an attenuated total reflection head.

6. The method of claim 1 wherein the FTIR energy spectrum is measured by a hand-held spectrometer.

7. The method of claim 1 wherein the passivation coating composition is a silane-containing coating composition.

8. The method of claim 7 wherein the silane-containing coating composition comprises:
   (a) 0.01 to 80 weight percent ureido silane, and/or hydrolyzate forms thereof;
   (b) 0.001 to 36 weight percent colloidal metal oxide and/or silica sol particles; and
   (c) remainder being water,
      wherein the weight percents are based on the total weight of the silane-containing coating composition.

9. The method of claim 7 wherein the silane-containing coating composition further comprises a fluorescence dye.

10. The method of claim 1 wherein the passivation coating composition is a metal alkoxide coating containing a metal selected from the group consisting of zirconium and titanium.

11. The method of claim 10 wherein the metal alkoxide is titanium tetraethoxide or zirconium tetraethoxide.

12. The method of claim 1 wherein the passivation coating composition is a fluorozirconic acid coating or fluorotitanic acid coating.

13. The method of claim 1 wherein the weight of the passivation coating composition is in the range of from about 5.4 to 5,400 milligrams per square meter.

14. The method of claim 1 wherein the substrate is selected from the group consisting of cold rolled steel, hot dip galvanized steel, electrogalvanized steel, aluminum, magnesium, zinc alloy and zinc coated steel.

15. The method of claim 1 wherein the substrate having the passivation coating composition is substantially dried before the FTIR measurement.

16. The method of claim 1 wherein the substrate having the passivation coating composition is a moving coil line.

17. The method of claim 16 wherein the moving coil line is stopped for a predetermined amount of an acquisition time during the FTIR measurement.

18. The method of claim 17 wherein the acquisition time is one second.

19. The method of claim 17 wherein the acquisition time is less than one second.

20. The method of claim 1 wherein the measuring the passivation coating composition weight per unit area on the substrate is done on a moving metal substrate without significantly interrupting the movement of the metal substrate.

* * * * *